United States Patent
White et al.

(10) Patent No.: US 9,414,855 B1
(45) Date of Patent: Aug. 16, 2016

(54) ANVIL KNIFE FOR ANASTOMOSIS TOOL

(75) Inventors: Nathan H. White, Palo Alto, CA (US); Michael P. Schaller, Palo Alto, CA (US); Luke W. Clauson, Redwood City, CA (US)

(73) Assignee: Cardica, Inc., Redwood City, CA (US)

( * ) Notice: Subject to any disclaimer, the term of this patent is extended or adjusted under 35 U.S.C. 154(b) by 2532 days.

(21) Appl. No.: 11/935,315

(22) Filed: Nov. 5, 2007

(51) Int. Cl.
*A61B 17/3207* (2006.01)

(52) U.S. Cl.
CPC .............................. *A61B 17/320783* (2013.01)

(58) Field of Classification Search
CPC ............... A61B 17/320758; A61B 17/320783; A61B 2017/320791
USPC ......... 606/159, 153, 167, 170, 171, 200, 219, 606/142; 604/22; 623/1.36; 227/175.1, 227/180.1
See application file for complete search history.

(56) References Cited

U.S. PATENT DOCUMENTS

| | | | |
|---|---|---|---|
| 3,636,955 A * | 1/1972 | Kurtz ............................ | 606/223 |
| 6,174,309 B1 * | 1/2001 | Wrublewski et al. ........... | 606/45 |
| 6,391,038 B2 | 5/2002 | Vargas et al. | |
| 6,447,525 B2 * | 9/2002 | Follmer et al. ................ | 606/159 |
| 6,916,328 B2 * | 7/2005 | Brett ............................. | 606/167 |
| 7,285,131 B1 | 10/2007 | Bombard et al. | |
| 7,722,548 B2 * | 5/2010 | Cervi ............................ | 600/564 |
| 2005/0159770 A1 * | 7/2005 | Divani et al. .................. | 606/200 |
| 2009/0187203 A1 * | 7/2009 | Corvi et al. ................... | 606/159 |

* cited by examiner

*Primary Examiner* — Jocelin Tanner
(74) *Attorney, Agent, or Firm* — Womble Carlyle Sandridge & Rice LLP

(57) ABSTRACT

A tool for treating a target vessel may include a longitudinally elongated anvil, a channel defined substantially longitudinally in the anvil, and a knife rotatable from a stowed position substantially completely within the channel to an active position in which at least part of the knife extends upward out of the channel, whereby rotation of the knife from the stowed position to the active position incises the target vessel from the inside out. A method of treating a target vessel having a wall may include providing a longitudinally elongated anvil, a channel defined substantially longitudinally in the anvil, and a knife rotatable into and out of the channel; rotating the knife from a stowed position substantially completely within the channel to an active position in which at least part of the knife extends upward out of the channel, wherein the rotating causes the knife to penetrate through the wall of the target vessel; translating the knife along the anvil to create an incision having a length; and rotating the knife from the active position to a withdrawal position substantially completely within the channel, wherein the rotating is in the same direction as the rotating the knife from the stowed position to the active position.

12 Claims, 2 Drawing Sheets

ANVIL KNIFE FOR ANASTOMOSIS TOOL

FIELD OF THE INVENTION

The invention relates to an anvil and knife configured to surgically incise a hollow vessel from the inside.

BACKGROUND

Surgical staplers, such as those used for vascular anastomosis, often include an anvil against which staples are deformed. As one example, U.S. patent application Ser. No. 10/151,441, filed on May 20, 2002, (the "'441 application"), which is hereby incorporated by reference in its entirety, described an anastomosis stapler including a staple holder and an anvil, where that anvil is inserted through the wall of a target vessel at or in proximity to the anastomosis site. The target vessel may be a coronary artery. The anvil may be inserted, from outside the target vessel, through a pre-existing incision in the wall of the target vessel into the lumen of the target vessel. Although that incision is large enough to accommodate entry of the anvil into the lumen of the target vessel, another opening in the target vessel may be necessary to allow for sufficient fluid communication between a graft vessel and the target vessel.

BRIEF DESCRIPTION OF THE DRAWINGS

The use of the same reference symbols in different figures indicates similar or identical items.

DETAILED DESCRIPTION

Figure 1:
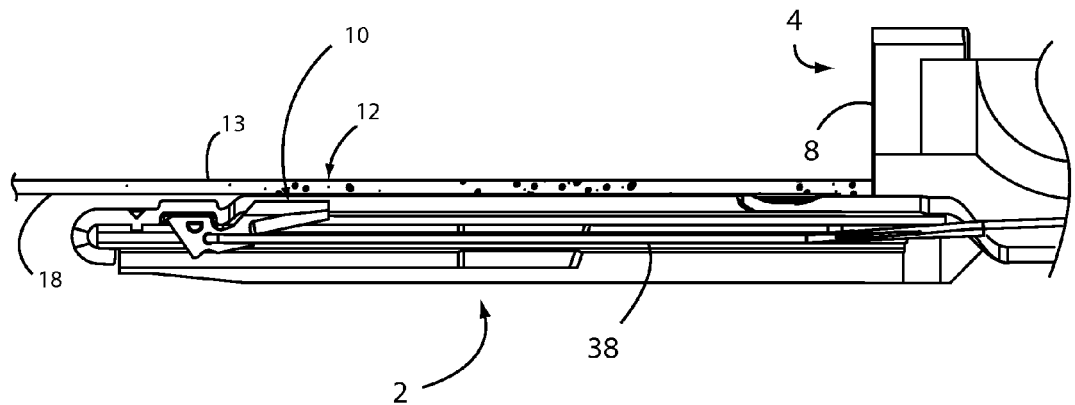
FIG. 1 is a side cross-section view of an anvil in a first configuration.

Referring to FIG. 1, an anvil 2 is shown. The anvil 2 may be part of an end effector of an anastomosis tool 4, or may be part of or connected to a different surgical instrument. As one example, the anvil 2 may be connected to a staple holder, as set forth in the '441 application. The length to width ratio of the anvil 2 may be substantially between 2:1 and 15:1. A different length to width ratio may be used, if desired. The anvil 2 may have a height and a width of 2 mm or less, advantageously about 1 mm or less, and a length of 2 to 15 mm, advantageously 5 to 12 mm. Alternately, the anvil 2 may be dimensioned differently. A tissue stop 8 may be included in the anvil, connected to the anvil 2, or included in another part of the anastomosis tool 4. The tissue stop 8 has a cross-sectional area greater than the anvil 2, such that upon insertion of the anvil 2 into a hollow vessel from the outside, the tissue stop 8 contacts the outer surface 13 of the vessel 12 to restrict further advancement of the anvil 2 into the vessel.

Figure 2:
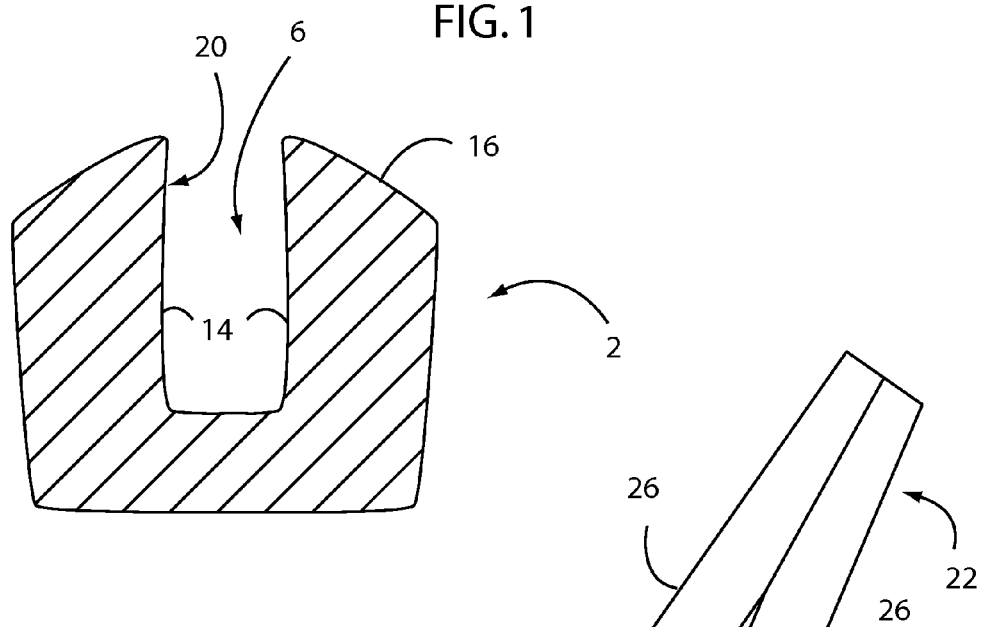
FIG. 2 is an end cross-section view of the anvil of FIG. 1.

Referring also to FIG. 2, the anvil 2 may be configured generally as set forth in the '441 application, where the anvil 2 is longitudinally elongated and includes a channel 6 defined substantially longitudinally therein. The channel 6 may extend along part or all of the anvil 2. The channel 6 may be generally rectangularly shaped, or may be shaped in any other suitable manner. Referring also to FIG. 1, a knife 10 is movable along at least part of the channel 6 to make an incision in the wall of the vessel 12. The knife 10 is narrower than the channel 6, such that the lateral walls 14 of the channel guide and/or laterally restrain motion of the knife 10 as the knife 10 translates along the channel 6. As used in this document, the terms "translate," "translates" and "translation" refers to motion in either the distal or proximal direction, whether or not the knife 10 or a portion thereof moves upward or downward during that motion. For convenience, the direction substantially perpendicular to the longitudinal centerline of the anvil 10 toward the wall of the vessel 12 may be referred to as "upward", and the opposite direction may be referred to as "downward". However, the positioning of the anvil 10 in use is not limited to an orientation in which these directions correspond to absolute directions measured relative to the ground. Similarly, for convenience, motion upward or downward may be referred to as "vertical" motion, and motion substantially parallel to the longitudinal centerline of the anvil 10 may be referred to as "horizontal" motion.

Each lateral wall 14 of the channel 6 may be substantially planar, curved, or may be shaped in any other suitable manner. Further, each lateral wall 14 may be oriented at an angle to vertical or substantially vertical. The lateral walls 14 may be formed such that the channel 6 is substantially bilaterally symmetrical, or may be fabricated to result in a channel 6 that is not bilaterally symmetrical. The anvil 10 includes a contact surface 16. In use, the contact surface 16 of the anvil 10 is placed substantially against the inner surface 18 of a target vessel 12. The contact surface 16 may have any suitable shape. The contact surface 16 may include one or more staple bending features (not shown) defined thereon. At least part of the contact surface 16 is bifurcated by the upper opening 20 of the channel 6, which extends along at least a portion of the contact surface 16 in a direction that may be substantially parallel to the longitudinal centerline of the anvil 10. The upper opening 20 may divide the contact surface 16 into symmetrical or asymmetrical sections. The upper opening 20 need not extend proximally any further than the tissue stop 8. However, the upper opening 20 may extend proximal to the tissue stop 8, if desired.

Figure 3:
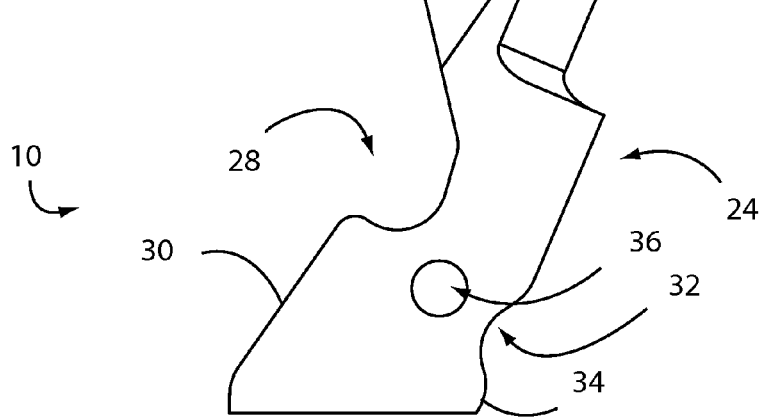
FIG. 3 is a side view of a knife used with the anvil of FIG. 1.

Referring to FIG. 3, an exemplary knife 10 is shown. The knife 10 is rotatable or otherwise movable from a stowed position in which it is substantially completely within the channel 6 in the anvil 2 (as shown in FIG. 1) to an active position in which at least a portion of the knife 10 extends upward out of the channel 6 in the anvil 2 (shown in FIGS. 4-5). The knife 10 may lie substantially in a single plane. That is, the knife 10 may be shaped such that a single plane extends through and substantially bisects the entire knife 10. Alternately, the knife 10 does not lie in a single plane. The knife 10 includes a cutting portion 22 that extends from a base 24. The cutting portion 22 may include at least one cutting edge 26, which may be beveled or otherwise sharpened. Advantageously, the cutting portion 22 may include two cutting edges 26, positioned on opposite sides of the cutting portion 22, lying in substantially the same plane, and angled relative to one another at any suitable angle. Alternately, the cutting edges 26 may be oriented differently relative to one another in any suitable manner. The base 24 of the knife 10 may include a first notch 28 defined therein on one side, below a cutting edge 26. The portion of the base 24 below the first notch 28 may be referred to as a first lobe 30. The base 24 of the knife 10 also may include a second notch 32 defined therein on the opposite side from the first notch 28, below the other cutting edge 26. The portion of the base 24 below the second notch 32 may be referred to as a second lobe 34. An aperture 36 may be defined in and/or completely through the base 24 of the knife 10, or in and/or completely through any other suitable portion of the knife 10. Referring also to FIG. 1, a cable 38 may be received through the aperture 36 to connect to the knife 10. The cable 38 may be flexible, partially flexible or rigid. The cable 38 may be fabricated from multiple filaments. Alternately, the cable 38 may be a monofilament cable, such as a high-tensile or spring temper stainless steel wire. The cable 38 extends proximally from the knife 10 along the channel 6 in the anvil 2. The cable 38 may be fixed to the knife 10. The cable 38 may extend through the aperture 36 such that both ends of the cable 38 extend proximally out of the anvil 2. The knife 10 may be free to rotate about the cable 38 extending through the aperture 36. Alternately, an end of the cable 38 may be attached to the knife 10 in any suitable manner. Alternately, the aperture 36 may be omitted, and the cable 38 may be connected to the knife 10 in a different manner. Alternately, the cable 38 may instead be a rod or any other suitable structure.

Figure 4:
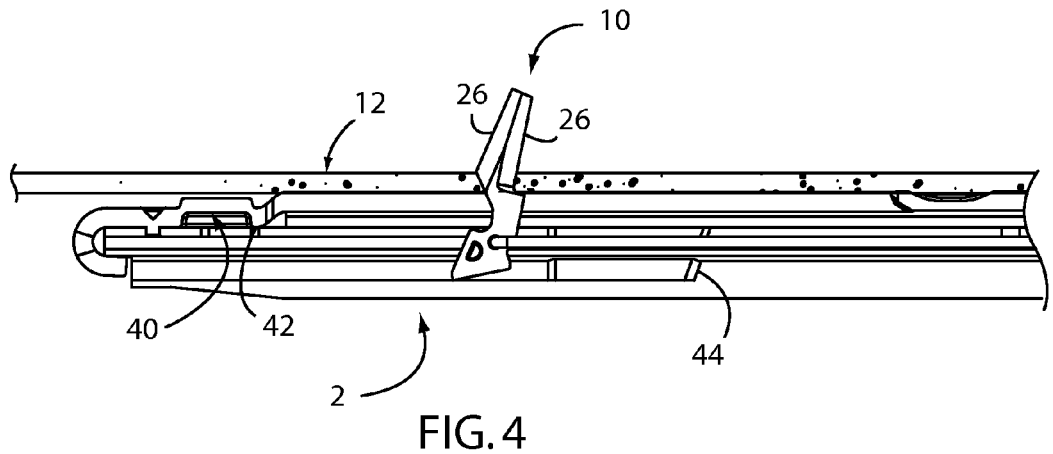
FIG. 4 is a side cross-section view of an anvil in a second configuration.

Referring also to FIG. 4, a receiving space 40 may be defined in the anvil 2, at a location that may be distal to the upper opening 20 of the channel 6, and oriented downward. The receiving space 40 may be located distal to a bump 42, which is also oriented downward relative to the contact surface of the anvil 2, and extends downward lower than the uppermost part of the receiving space 40. The bump 42 may define the proximal end of the receiving space 40. The receiving space 40 is shaped and sized to receive the first lobe 30 of the knife 10, as described in greater detail below. Proximal to the receiving space 40, a step 44 is defined in the anvil 2, which extends upward relative to the bottom surface of the channel 6 in the anvil 2. The step 44 may extend any suitable distance in the proximal direction. The upper surface of the step 44 is spaced apart from the contact surface 16 a distance great enough to allow the knife 10 to be received above the step 44 and below the contact surface 16, as described in greater detail below.

Operation

Initially, the knife 10 is in the stowed position, and may be substantially restrained from translation. In the stowed position, substantially all of the knife 10 is within the channel 6 in the anvil 2. At least part of the first lobe 30 may be positioned at least partially within the receiving space 40; the edge of the first lobe 30 may be parallel to and/or in contact with the upper surface of the receiving space 40. The bump 42 is located proximal to the first lobe 30. Engagement between the bump 42 and the first notch 28 in the knife 10, and between the first lobe 30 and the receiving space 40, may be sufficient to maintain the knife 10 in place in the stowed position. Alternately, the knife 10 may be maintained in the stowed position in any other suitable manner. The anvil 2 may be inserted into the lumen of the vessel 12 through an opening or incision (not shown) in the wall of that vessel 12, from the outside in. When the knife 10 is in the stowed position, the cutting edges 22 of the knife 10 are within the channel 6 in the anvil 2, such that they do not incise tissue during insertion of the anvil 2 into the vessel 2.

Referring also to FIG. 4, the cable 38 is then moved proximally. The first lobe 30 is restricted against sliding proximally in response by contact with the bump 42. The aperture 36 in the knife 10, which receives the cable 38, is located below the lowest point of the bump 42. Consequently, proximal motion of the cable 38 results in a moment about the bump 42, causing the first lobe 30 to rotate out of the receiving space 40. The first notch 28 in the knife 10 is shaped and sized to allow rotation of the knife 10 around the bump 42. The first notch 28 and the bump 42 may each be smoothly curved to facilitate such rotation. Contact between the bump 42 and the first lobe 30, as well as the shape of the bump 42 and the first lobe 30 and the moment applied to the knife 10, also cause the knife 10 to rotate about the aperture 36 as the cable 38 translates the aperture 36 proximally. The cable 38 or other structure may extend into and/or through the aperture 36, such that rotation about the aperture 36 is also rotation about the portion of the cable 38 or other structure that extends into and/or through the aperture 36. As the first lobe 30 rotates out of the receiving space 40, the cutting portion 22 of the knife 10 rotates upward out of the upper opening 20 of the channel 6, moving above the contact surface 16 of the anvil 2. As the cutting portion 22 of the knife 10 moves upward, a cutting edge 26 of the knife 10 incises the wall of the vessel 12 from the inside out. When rotation of the knife 10 is complete, the knife 10 is in the active position, with the knife 10 extending through the wall of the vessel 12 and a cutting edge 26 of the knife 10 oriented in the direction in which the knife 10 is to be moved, which as shown is the proximal direction.

Figure 5:
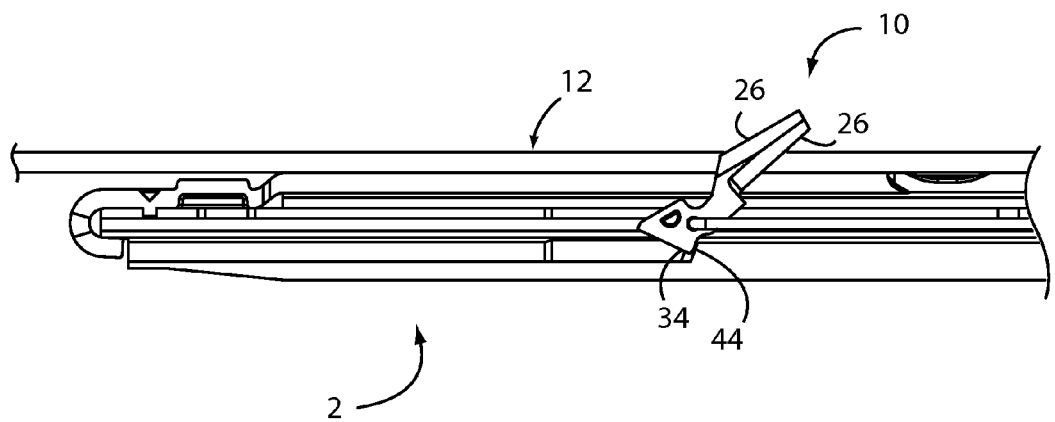
FIG. 5 is a side cross-section view of an anvil in a third configuration.

The cable 38 continues to move proximally, pulling the knife 10 proximally as a result. The channel 6 in the anvil 2 may be slightly wider than the knife 10, providing lateral stability for the knife 10 by substantially preventing the knife 10 from moving laterally during its proximal motion. Further, the bottom corner of the first lobe 30 may contact the bottom surface of the channel 6 to maintain a substantially constant cutting angle between the knife 10 and the bottom surface of the channel 6 as it translates along the channel 6 in the anvil 2. As the knife 10 moves proximally, at least one cutting edge 22 cuts the wall of the vessel 12. Where that vessel 12 is a blood vessel, the cut made by the knife 10 is an arteriotomy. The length of the arteriotomy is related to the distance along which the knife 10 is translated. This distance is controlled by the distance along which the cable 38 is moved proximally, as well as the internal configuration of the anvil 2. Referring also to FIG. 5, as the knife 10 continues to move proximally, the second lobe 34 of the knife 10 contacts the step 44 defined in the channel 6 of the anvil 2. As the cable 38 continues to move proximally, the second lobe 34 of the knife 10 cannot translate further proximally due to contact with the step 44. However, the knife 10 can rotate about the aperture 36 defined in the knife 10. The aperture 36 is located above the step 44 of the anvil 2. As a result, continued proximal motion of the cable 38 creates a moment, causing the knife 10 to rotate about the aperture 36, which results in the motion of the tip of the knife 10 proximally and downward into the channel 6 of the anvil 2. As the knife 10 rotates downward into the channel 6, at least one cutting edge 26 incises the wall of the vessel 12 proximal to the step 44. In this way, a particular distance of travel of the cable 38 creates an arteriotomy in the vessel 12 that is longer than that particular distance of travel of the cable 38. That is, the cutting edge 26 extends a distance away from the aperture 36, and that distance along the cutting edge 26 is cut by the knife 10 as the knife 10 rotates downward into the channel 6, where that distance is greater than the incremental distance that the cable 38 travels to create that rotation of the knife 10. The second notch 32 is shaped to allow rotation of the knife 10 relative to the step 44 in the anvil 10 without interference with the step 44. As the knife 10 rotates about the aperture 36, the second notch 32 rotates about the edge of the step 44, allowing the knife 10 to smoothly rotate downward into the channel 6. When the knife 10 rotates about the aperture 36, the first lobe 30 of the knife 10 also rotates distally and upward, remaining within the channel 6 of the anvil 2.

Figure 6:
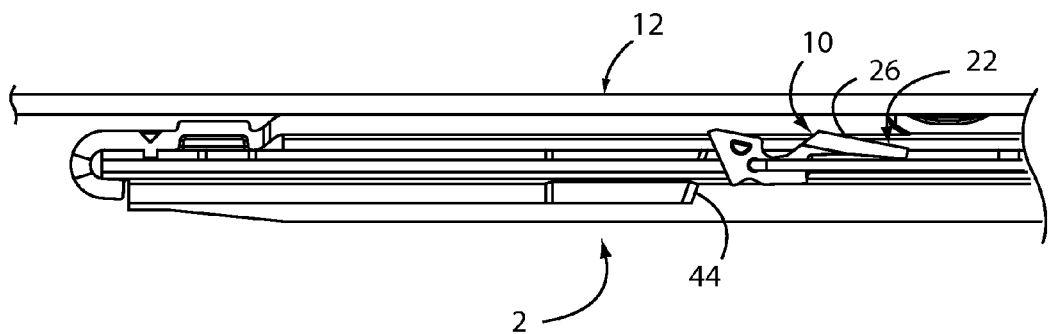
FIG. 6 is a side cross-section view of an anvil in a fourth configuration.

Referring also to FIG. 6, rotation of the knife 10 about the aperture 36 continues until the cutting edges 22 are positioned entirely within the channel 6 in the anvil 2. Advantageously, the entire knife 10 moves into the channel 6 in the anvil 2. As shown in FIG. 6, motion of the knife 10 is then complete, with the knife 10 having rotated to a withdrawal position from the active position. When the knife 10 is in the withdrawal position, the cutting edges 22 of the knife 10 are within the channel 6 in the anvil 2, such that they do not incise tissue during withdrawal of the anvil 2 from the vessel 12. The direction of rotation of the knife 10 from the stowed position to the active position is the same as the direction of rotation of the knife 10 from the active position to the withdrawal position.

A graft vessel may be connected to the vessel 12 in any suitable manner, before, during or after making the incision in the wall of the vessel 12 as described above. As one example, an end of the graft vessel may be stapled to the wall of the vessel 12, as set forth in U.S. patent application Ser. No. 10/151,441, filed on May 20, 2002, which is hereby incorporated by reference in its entirety. The incision in the wall of the vessel 12 allows blood or other fluid, depending on the vessel 12, to flow between the vessel 12 and the graft. Optionally, the anvil 2 and knife 10 described above may be used simply to create an arteriotomy in the wall of the vessel 12, without connecting a graft to the vessel 12.

While the invention has been described in detail, it will be apparent to one skilled in the art that various changes and modifications can be made and equivalents employed, without departing from the present invention. It is to be understood that the invention is not limited to the details of construction, the arrangements of components, and/or the method set forth in the above description or illustrated in the drawings. Statements in the abstract of this document, and any summary statements in this document, are merely exemplary; they are not, and cannot be interpreted as, limiting the scope of the claims. Further, the figures are merely exemplary and not limiting. Topical headings and subheadings are for the convenience of the reader only. They should not and cannot be construed to have any substantive significance, meaning or interpretation, and should not and cannot be deemed to indicate that all of the information relating to any particular topic is to be found under or limited to any particular heading or subheading. Therefore, the invention is not to be restricted or limited except in accordance with the following claims and their legal equivalents.

What is claimed is:

1. A surgical tool for treating a target vessel, comprising:
   a longitudinally elongated anvil;
   a channel defined substantially longitudinally in said anvil, and
   a knife rotatable about an axis from a stowed position in which said knife is substantially completely within said channel to an active position in which at least part of said knife extends upward out of said channel, whereby rotation of said knife from said stowed position to said active position incises the target vessel from the inside out wherein said axis is movable longitudinally along said anvil; and
   wherein said knife is rotatable about said axis from said active position to a withdrawal position in which said knife is substantially completely within said channel, wherein said withdrawal position is longitudinally spaced apart from said stowed position.

2. The surgical tool of claim 1, incorporating by reference all of the elements of that claim, wherein said withdrawal position is proximal to said stowed position.

3. The surgical tool of claim 2, incorporating by reference all of the elements of that claim, wherein said knife rotates in the same direction from said stowed position to said active position as said knife rotates from said active position to said withdrawal position.

4. The surgical tool of claim 1, incorporating by reference all of the elements of that claim, wherein said knife includes a cutting portion, and wherein said cutting portion is oriented substantially proximally when said knife is in said withdrawal position.

5. The surgical tool of claim 1, incorporating by reference all of the elements of that claim, wherein said knife includes an aperture defined therein, and wherein said knife is rotatable about said aperture.

6. The surgical tool of claim 5, incorporating by reference all of the elements of that claim, further comprising a cable extending into said aperture.

7. The surgical tool of claim 1, incorporating by reference all of the elements of that claim, wherein said knife includes two cutting edges, said cutting edges positioned on opposite sides of said knife.

8. The surgical tool of claim 1, incorporating by reference all of the elements of that claim, further comprising two notches defined in said knife, said notches defined in opposite sides of said knife.

9. The surgical tool of claim 1, incorporating by reference all of the elements of that claim, wherein said channel has a bottom surface; further comprising a step extending upward from said bottom surface of said channel.

10. The surgical tool of claim 1, incorporating by reference all of the elements of that claim, wherein said knife is rotatable upward and proximally.

11. The surgical tool of claim 1, incorporating by reference all of the elements of that claim, further comprising a bump extending downward relative to an upper surface of said anvil, wherein said knife is movable into contact with said bump to cause said knife to rotate from said stowed position to said active position.

12. The surgical tool of claim 1, incorporating by reference all of the elements of that claim, wherein said knife includes a cutting portion, and wherein said cutting portion is oriented substantially proximally when said knife is in said stowed position.

* * * * *